United States Patent [19]
Utermohlen et al.

[11] Patent Number: 5,948,617
[45] Date of Patent: Sep. 7, 1999

[54] METHODS OF IN SITU HYBRIDIZATION

[75] Inventors: Joseph G. Utermohlen; David W. Sammons, both of Tucson, Ariz.

[73] Assignee: BioSpeparations, Inc., Tucson, Ariz.

[21] Appl. No.: 08/874,270

[22] Filed: Jun. 13, 1997

[51] Int. Cl.⁶ .............................. C12Q 1/68; C07H 21/04
[52] U.S. Cl. ................................. 435/6; 435/5; 435/40.5; 435/40.52; 435/455; 435/325; 536/23.1; 536/24.3; 536/24.31
[58] Field of Search .................. 435/6, 5, 40.5, 435/40.52, 455, 325; 536/231, 24.3, 24.31; 935/78

[56] References Cited

U.S. PATENT DOCUMENTS

| | | | |
|---|---|---|---|
| 4,302,204 | 11/1981 | Wahl et al. ........................ | 23/230.3 |
| 4,358,535 | 11/1982 | Falkow et al. ..................... | 435/5 |
| 4,647,529 | 3/1987 | Rodland et al. .................... | 435/6 |
| 4,689,294 | 8/1987 | Boguslawski ...................... | 435/6 |
| 4,886,741 | 12/1989 | Schwartz .......................... | 435/5 |
| 4,888,278 | 12/1989 | Singer et al. ..................... | 435/6 |
| 5,132,207 | 7/1992 | Kohne et al. ...................... | 435/6 |
| 5,225,326 | 7/1993 | Bresser et al. .................... | 435/6 |
| 5,232,831 | 8/1993 | Milliman et al. ................... | 435/6 |
| 5,316,906 | 5/1994 | Haugland et al. ................... | 435/4 |
| 5,447,841 | 9/1995 | Gray et al. ....................... | 435/6 |
| 5,506,098 | 4/1996 | Zarling et al. .................... | 435/6 |
| 5,512,436 | 4/1996 | Stone ............................. | 435/6 |
| 5,521,061 | 5/1996 | Bresser et al. .................... | 435/517 |
| 5,750,340 | 5/1998 | Kim et al. ........................ | 435/6 |

FOREIGN PATENT DOCUMENTS

| | | |
|---|---|---|
| WO90/02204 | 8/1990 | WIPO . |
| WO95/03431 | 2/1995 | WIPO . |
| WO96/31626 | 10/1996 | WIPO . |

OTHER PUBLICATIONS

"Fluorescent in situ Hybridization for the Diagnosis of Genetic Disease at Postnatal, Prenatal, and Preimplantation Stages" by Darren K. Griffin *International Revew of Cytology* vol. 153, pp. 1–35 (1994).

"A Rapid FISH Techique for Quantitative Microscopy" by F.M. Haar, et al. *Biotechniquest Research Reports* vol. 17, No. 2, pp. 346–353 (1994).

"Rapid Detection of Chromosome Aneuploidies in Uncultered Amniocytes by Using Fluorescence In Situ Hybridization (FISH)" by Katherine Klinger, et al. *Am. J. Human Genet.* vol. 51, pp. 55–65 (1992).

"Detection of Aneuploidy Involving Chromosomes 13, 18 or 21 by Fluorescence in Situ Hybridization (FISH) to Interphase and Metaphase Amniocytes" by Wen–Lin Kuo, et al. *Am. j. Human Genet.* vol. 49, pp. 112–119 (1991).

"Rapid Prenatal Diagnosis of Chromosomal Aneuploidies by Fluorescence in Situ Hybridization: Clinical Experience with 4,500 Specimens" by Brian E. Ward, et al. *Am. J. Human Genet.* vol. 52, pp. 854–865 (1993).

"Fast Hybridization Solution for the Detection of Immobilized Nucleic Acids" by Te–Tuan Yang, et al. *Biotechniques Research Reports*, vol. 18, No. 3, pp. 498–503 (1995).

"ExpressHyb Hybridization Solution" by Clontech Laboratories, Inc. *Catalog #8015 Product Protocol*, pp. 1, 5,7,9,and 11.

"Cy3™—Chromosome X Human Alpha–Satellite Specific Probe Cat. No. A6300X" by Biological Detection Systems, Inc. *Cyprobe Pamphlet*.

(List continued on next page.)

*Primary Examiner*—Carla J. Myers
*Attorney, Agent, or Firm*—David G. Rosenbaum; Sonnenschein, Nath and Rosenthal

[57] ABSTRACT

A method and single solution denaturation and hybridization solution useful with synthetic oligonucleotide probes for hybridizing DNA or RNA sequences by in situ hybridization. The inventive protocol employs synthetic oligonucleotide probes and a glycerol-based hybridization solution which is particularly useful in fluorescence labeling of chromosomes X, Y, 13, 18 and 21 in human lymphocytes, amniocytes and metaphase chromosomes, with the label being sufficiently stable to permit archival storage of the labeled sample for later hybridization or analysis.

10 Claims, 14 Drawing Sheets

OTHER PUBLICATIONS

"Formamide" by Fisher Scientific, Inc. *Material Safety Data Sheet*, pp. 1–4 (1995).

"Rapid Hybridization Protocol for Direct–Labeled (FITC or Texas Red) Satellite DNA Probes" by Oncor, Inc. *Oncor Detection Kit: Rapid Chromosome In Situ Hybridization System*, Edition 1, pp. 1–13 (Oct. 1993).

"Spectrum CEP Direct Chromosome Enumeration System" by Imagentics, Inc. *Imagentics Pamphlet* (*Prodecural Kit*).

"Nucleic Acid Hybridization: From Research Tool to Routine Diagnostic Method" by A.C. Syvänen *Medical Biology* (*Review Article*), vol. 64, pp. 313–324 (1996).

"A Manual for Genetic Engineering, Advanced Bacterial Genetics" by Ronald W. Davis, et al. *article from Cold Spring Harbor Laboratory* (1980).

"Molecular Cloning, A Laboratory Manual" by T. Maniatis, et al. *article from Cold Spring Harbor Laboratory*, pp. 338–389 (1982).

"AproProbe™ Plus" by Aprogenex, Inc. *Aprogenex pamphlet*.

"Renaturants and Preservatives", 1 page pamphet.

"Vysis FISH Technology and Nucleic Acid Probes" by Vysis, Inc. (Mar. 1997).

The Boehringer Mannheim Catalog, pp. 14–17, 1992.

Singer et al. Bio Techniques, 4: 230–243, 1986.

Parry et al. In DNA Cloning 1: Core Techniques, A Practical Approach. Glover et al. editors, IRL Press, New York, pp. 151–152, 1995.

METHODS OF IN SITU HYBRIDIZATION

BACKGROUND OF THE INVENTION

The present invention relates generally to in situ hybridization methods and hybridization buffers for labeling of interphase nuclei. More particularly, the present invention relates to a protocol and buffer which is particularly useful in conjunction with synthetic oligonucleotide probes for hybridizing DNA or RNA sequences by fluorescence in situ hybridization ("FISH"). In accordance with the preferred embodiments of the present invention, the inventive FISH protocol employs synthetic oligonucleotide probes having less than about 75 bases, preferably between about 15–50, most preferably between about 25 and 35 bases, and a single solution denaturation and hybridization buffer solution which permits the entire FISH protocol to be completed within time periods suitable for clinical diagnostic application. The present invention has been found particularly useful in fluorescence labeling of chromosomes X, Y, 13, 18 and 21 in human lymphocytes and amniocytes using synthetic oligonucleotide probes. Additionally, the present invention includes a methodology for conducting multiple, repeat rounds of FISH analysis, using different probe sets on the same sample. This repeat FISH methodology ("ReFISH") permits a sample to be subjected to a first FISH analysis with one probe then subsequently subjected to FISH analysis with a different probe. In all aspects of the present invention, the criteria for success included: 1) ease of procedure, 2) reliability, 3) hybridization specificity, 4) hybridization efficiency, 5) brightness of the fluorescence signal, 6) stability of the labeled hybrid, and 7) conservation of the cellular and nuclear morphology.

Conventional FISH technology is based on formamide chemistry for DNA denaturation, hybridization buffers, and post-hybridization washes. (Cremer T. Landegent J. Brueckner A, Scholl H P, Schardin M, Hager H D, Devilee P. Pearson P. van der Ploeg M. (1986), "Detection of chromosome aberrations in the human interphase nucleus by visualization of specific target DNAs with radioactive and non-radioactive in situ hybridization techniques: diagnosis of trisomy 18 with probe L .84," Hum. Genet 74:346–352; Pinkel D, Straume T. Gray J W. (1986) "Cytogenetic analysis using quantitative, high-sensitivity, fluorescence hybridization," Proc Natl Acad Sci USA 83:2934–2938). The entire procedure includes multiple steps for sample denaturation, hybridization and post-hybridization washes. This process often takes hours to yield a fluorescent label with a signal intensity sufficient for routine chromosome enumeration. Although some recent improvements of formamide-based FISH have been introduced, for example the use of co-denaturation of probes and sample and the elimination of formamide in the post hybridization washes (Abati A, Sanford J. Fetsch P. Marincola F. Wolman S. (1995) "Fluorescence in situ hybridization (FISH): a user's guide to optimal preparation of cytologic specimens," Diagnostic Cytopathology 13:5:486–492), the chemistry of the hybridization reaction is still based on formamide. Known disadvantages of formamide are that it reduces the kinetics of hybridization (Kourilsky Ph. Leidner J. Tremblay. 1971 "DNA-DNA hybridization on filters at low temperature in the presence of formamide or urea,. Biochimie 53:1111–1114), oxides easily, and is a known teratogen.

Currently, most clinical laboratories use FISH kits available from the following commercial sources: Oncor, Inc., Rapid Chromosome In Situ Hybridization System: Edition 1, October 1993, or Vysis, Inc. Both the Oncor and the Vysis probes are biological probes and the kit protocols employ formamide-based hybridization solutions. Another current kit for conducting FISH is available from Aprogenex, Inc. and is sold under the trademark APROPROBE PLUS. The APROPROBE PLUS FISH kit utilizes synthetic oligonucleotide fluorophore-labeled probes specific for the centromeric region of human chromosomes X, Y, 13/21 and 18 and the mRNA of gamma globin. The hybridization solution provided with the APROPROBE PLUS FISH kit is also formamide-based. See, also, Bresser, et al., U.S. Pat. No. 5,225,326, which teaches the use of formamide-based hybridization solution with oligonucleotide probes.

Non-formamide-based hybridization solutions for conducting FISH analysis are known in the art, as more fully disclosed in co-pending U.S. patent application Ser. No. 08/418,704, filed Apr. 7, 1995, published as International Application WO 96/31626, published on Oct. 10, 1996, which discloses use of a glycerol and dextran sulfate hybridization buffer for FISH labeling of human chromosomes using clone probes. However, when the teachings of International Application WO 96/31626, were followed using synthetic oligonucleotide DNA probes, such those available in the APROPROBE PLUS FISH Kit (Aprogenex, Inc.) or those disclosed in International Application 96/00234, published Jan. 4, 1996, clinically adequate labeling of the human chromosomes was not obtained. International Application WO 96/31626, published Oct. 10, 1996, is hereby incorporated by reference as to the teaching of a glycerol-based hybridization solution and the use of a glycerol-based hybridization solution with biological DNA probes. International Application 96/00234, published Jan. 4, 1996, is hereby incorporated by reference as teaching synthetic oligonucleotide clone probes specific for human chromosomes X, Y, 13, 18 and 21 useful with the present invention.

It was found necessary, therefore, to modify the glycerol-based hybridization methodology taught in International Application WO 96/31626, to adapt it for use with synthetic oligonucleotide DNA probes. Specifically, it was found that reducing the hybridization temperature from 55° C. to between 37 and 47° C., changing the sodium ion concentration in the wash, and reducing the wash temperature from 65° to a temperature which was substantially the same as the hybridization temperature, i.e., between 37 and 47° C., yielded acceptable specific binding and retention of the fluorophore labeled synthetic oligonucleotide probe to human chromosomes X, Y, 13, 18 and 21 in lymphocytes, amniocytes, and metaphase chromosomes. In accordance with the best mode of the present invention, however, it was found that while the bound fluorescence signal was acceptable, the signal was not conserved sufficiently to achieve an acceptable duration of the fluorescence signal. It was further discovered that the addition of dithiothreitol to the hybridization buffer achieved a prolonged duration of the bound fluorescence signal and permitted the labeled samples to be archival stored and analyzed at a later time.

For each of the inventive FISH protocols, the chromosome-labeling process was completed within 90 minutes. The inventive processes are based upon a unique formamide-free hybridization chemistry that accelerates the probe-to-target annealing reaction without compromising hybridization efficiency, specificity, or cellular and nuclear morphology. The inventive FISH processes use synthetic oligomeric probes with sequences derived from the alpha satellite regions of human chromosomes X, Y, 13, 18, and 21. Hybridization specificity and efficiency, and chromosomal target were retained through the repetitive FISH processing on the same sample. The inventive formamide-free FISH chemistry is readily adapted for use with different cell types. The simple and rapid methods developed with this chemistry work with either lymphocytes, uncultured amniocytes or with metaphase chromosomes, and with cells fixed by different methods. The inventive ReFISH process introduces the possibility of FISH analysis for multiple chromosome targets with a sample that is small or otherwise limited by generating simple patterns for each analysis, without the need to have complex mixtures of different probes. This avoids the interpretation of more complex signal patterns when multiple-target probe mixtures are used in a single reaction. Another advantage of ReFISH is that archived samples can be reexamined by FISH at a later date, i.e., several weeks or even months later, either for re-confirmation or with another probe set that was not requested or available at the time of initial testing.

SUMMARY OF THE INVENTION

A primary objective of the present invention is to provide a rapid protocol to label chromosomes in interphase nuclei, amniocytes and metaphase chromosomes by fluorescence in situ hybridization (FISH) without using formamide chemistry. The inventive FISH processes herein described are based upon a unique hybridization chemistry that is formamide free. This novel methodology preserves cellular and nuclear morphology during the denaturation and hybridization steps, while yielding a target-specific signal of high intensity in less than one hour for most cells. To demonstrate the efficiency of this formamide-free hybridization method, we present a simple FISH protocol using lymphocytes and uncultured amniocytes (Klinger K, Landes G. Shook D, Harvey R. Lopez L, Locke P. Lerner T. Osathanondh R. Leverone B. Houseal T. Pavelka K, Dackowski W. (1992), "Rapid detection of chromosome aneuploidies in uncultured amniocytes by using fluorescence in situ hybridization (FISH)," *Am J Hum Genet* 51:55–65; Bryndorf T. Christensen B. Vad M, Parner J. Brocks V, Phillip J. (1997) "Prenatal detection of chromosome aneuploidies by fluorescence in situ hybridization: experience with 2000 uncultured amniotic fluid samples in a prospective preclinical trial," *PrenatDiagn* 17:333–341). The inventive protocol was developed with the objective of simplifying the whole FISH labeling process, using a minimal number of steps for sample preparation, fixation, denaturation, hybridization, and post-hybridization washing.

Another objective of the present invention is to adapt the inventive FISH protocol to permit a repetitive FISH process, referred to as ReFISH (repeat FISH). ReFISH allows analysis of the same sample, same cell or even the same chromosome spread with different probes. Thus, a single sample is subjected to several subsequent rounds of FISH analysis. Data are presented showing that lymphocytes can be processed through four rounds of FISH (using different probe sets for each round) without affecting the hybridization efficiency of the targeted chromosomes, the signal intensity of label for each round of FISH, and the cellular and nuclear morphology.

It is a further objective of the present invention to conduct FISH in the presence of a formamide-free hybridization buffer.

It is a still further objective of the present invention to conduct FISH in the presence of a glycerol based hybridization buffer and in the presence of a synthetic oligonucleotide probe having from less than about 75 bases, preferably between 15 and 50, and most preferably between 25 and 35 bases, denaturing the cellular DNA by heating the sample to about 100° C. for about 1.5 min, hybridizing the probe and the sample at 42° C. for between about 5 to 30 min, for lymphocyte samples, or about 75 min. for uncultured amniocyte samples, and about 30 to 90 min. for metaphase chromosome spreads, and washing the post-hybridization sample to remove non-specifically bound probe and retain specifically bound probe.

It is another objective of the present invention to provide a FISH methodology for glycerol-based hybridization of synthetic oligonucleotide DNA probes specific for the centromeric regions of target chromosomes X, Y, 13 or 21, and 18, or a probe for a specific locus on chromosome 21.

It is a further objective of the present invention to provide an improved FISH methodology for hybridizing synthetic oligonucleotide DNA probes utilizing a glycerol-based hybridization buffer wherein the optimum temperature of hybridization kinetics is calculated according to the formula:

$$T_{hyb}=[(16.6 \log (Na^+)+0.41(\% G+\% C)+81.5)-500/L]-X$$

where, $Na^+$ is equal to the concentration of sodium cations, % G is equal to the percent of guanine bases in the synthetic oligonucleotide probe or target DNA sequence and % C is equal to the percent of cytosine bases in the synthetic oligonucleotide probe, or target DNA sequence, where X is an integer between 18 and 30. L is the number of nucleic acids in one of the probe and target sequence.

It is a further objective of the present invention to provide an improved FISH methodology for hybridizing synthetic oligonucleotide probe wherein the temperature of hybridization is substantially the same as the post-hybridization wash temperature.

These and other objects, features and advantages of the present invention are more readily understood by those of ordinary skill in the art from the following more detailed description of the preferred embodiments of the present invention taken with reference to the accompanying figures.

DETAILED DESCRIPTION OF THE PREFERRED EMBODIMENTS

Figure 1:
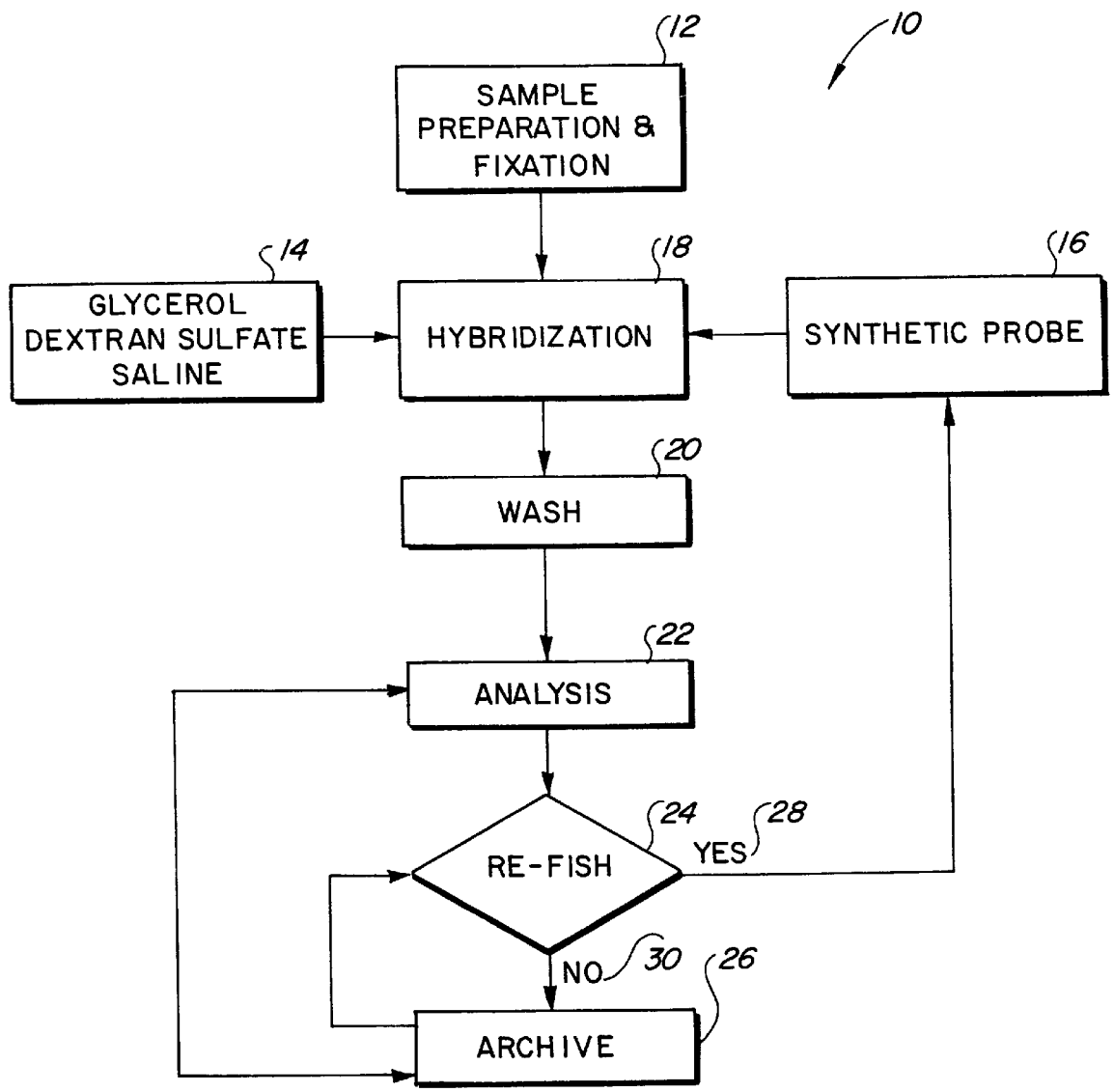
FIG. 1 is a process flow diagram illustrating the inventive FISH methodology.

Replication of International Application WO 96/31626: Solution G, Denaturation and Hybridization Conditions with Aprogenex Clone Probes From International Application WO 96/31626 the denaturation and hybridization solutions and conditions of denaturation, hybridization and washing were followed and synthetic probes from the Aprogenex APROBE PLUS FISH kit were tested as follows. Two probe and hybridization solutions were made. Sample A was made by adding 0.5 $\mu$l of Aprogenex XY probe to 10 $\mu$l of Solution G from International Application WO 96/31626 (20% glycerol (v/v), 10% dextran sulfate (w/v) and 0.9% NaCl (w/v)). Sample B was made as 0.1× of Sample A by adding 0.5 $\mu$l of Aprogenex XY probe to 100 $\mu$l of Solution G. 15 $\mu$l of Sample A was added to a glass slide and covered with a circular coverslip. 15 $\mu$l of Sample B were added to another glass slide and covered with a circular coverslip. Both slides were heated at 100° C. for 1.5 min., then at 55° C. for 30 min., washed for 30 sec. In 0.15% NaCl (w/v) at 65° C. and 0.18% NP-40 (v/v), followed by a second 30 sec. wash in 0.15% NaCl (w/v), 0.18% NP-40 (v/v) (0.026 M $Na^+$) at 65° C. The slides were then stained with 4,6-diamidino-2-phenylindole (DAPI) at 20 ng/ml and analyzed for bound fluorescence signal. It was determined that there was inadequate bound signal present on either slide to be diagnostically useful.

Replication of international Application WO 96/31626: Solution G, Inventive Denaturation and Hybridization Conditions with Aprogenex Clone Probes 1.5 $\mu$g/$\mu$l of Aprogenex XY probe in Solution G from International Application WO 96/31626 (20% glycerol (v/v), 10% dextran sulfate (w/v) and 0.9% NaCl (w/v)) was added to a glass slide and covered with a circular coverslip. The sample slide was then heated at 100° C. for 1.5 min to denature the chromosomal DNA, then hybridized at 47° C. for 30 min followed by washing in accordance with the Aprogenex APROBE PLUS wash protocol incorporated by reference. The resulting sample was then stained with DAPI (50 ng/ml) and analyzed for bound fluorescence signal. It was determined that the hybridization efficiency was approximately 97.4% with moderate bound signal (scored as 2–3 on a scale of 1 to 5).

To then determine the effect of the wash type on hybridization, the conductivity of the Aprogenex APROBE PLUS washes was measured and wash solutions based upon the wash solution system taught in International Application WO 96/31626, i.e., NaCl and NP-40, was devised. It was found that the conductivity of the Aprogenex Wash A was measured at 3500 $\mu$S and the conductivity of Aprogenex Was B was measured at 2600 $\mu$S. An NaCl and NP-40 solution having conductivity of about 3500 $\mu$S was made by admixing 0.35 M NaCl with 0.15% NP-40 (hereinafter "Saline Wash A) and a NaCl and NP-40 solution having conductivity of about 4800 $\mu$S was made by admixing 0.035 M NaCl with 0.15% NP-40 (hereinafter "Saline Wash B"). The hybridization reaction was carried out as described above in this section and the hybridized sample was washed in Saline Wash A for 3 min at 42° C., followed by four washes in Saline Wash B, with each wash being for 30 sec at 42° C. It was determined that the glycerol-based hybridization solution was not dependent on the Aprogenex Wash A and Wash B solutions, and moderate bound signal was conserved using the Saline Wash A and Saline Wash B protocol.

Replication of International Application WO 96/31626: Solution G Plus DDT, Inventive Denaturation and Hybridization Conditions with Aprogenex Clone Probes In the foregoing example, while there was moderate bound signal obtained using the inventive denaturation and hybridization conditions with the synthetic oligonucleotide probes and the glycerol-based hybridization medium, it was found that the duration of the signal was transient. Accordingly, a methodology was devised to stabilize the bound signal when using a glycerol-based hybridization solution in which a reducing agent, such as dithiothreitol (DTT), dithioerythritol, mercaptoethanol, or tris (2-carboxyethyl)phosphine is added to the glycerol-based hybridization solution.

1.5 $\mu$g/$\mu$l of Aprogenex XY probe in Solution G from International Application WO 96/31626 (20% glycerol (v/v), 10% dextran sulfate (w/v) and 0.9% NaCl (w/v)) and 100 mM DTT was added to a glass slide and covered with a circular coverslip. The sample slide was then heated at 100° C. for 1.5 min to denature the chromosomal DNA, then hybridized at 42° C. for 30 min followed by washing in Saline Wash A for 3 min at 42° C., followed by four washes in Saline Wash B, with each wash being for 30 sec at 42° C. The resulting sample was then stained with DAPI (50 ng/ml) and analyzed for bound fluorescence signal and duration of signal. It was determined that the signal was bound and, when compared to a control sample, without DTT, only the sample processed with the DTT had a signal which did not quickly fade. To determine whether the presence of DTT drove hybridization, subsequent experiments were conducted using a hybridization buffer without glycerol, but with only dextran sulfate, saline and DTT, and it was found that the absence of the glycerol component from the hybridization buffer did not drive hybridization of the synthetic oligonucleotide clone probes. Further experiments tested whether DTT, with only glycerol and saline, and without dextran sulfate drove hybridization. It was found that the absence of dextran sulfate from the hybridization medium, in the presence of DTT, did drive hybridization of the synthetic oligonucleotide clone probes.

The following summarizes general protocols for in situ hybridization and ReFISH of lymphocytes, amniocytes and metaphase spreads.

Protocol 1: Lymphocyte In-Situ Hybridization

The cell preparation protocols and FISH process used with lymphocytes are described below. The methods of cell post-fixation differ, but all other steps are the same. The post-fixation process referred to as Protocol 1A is a 15 second treatment in Ethanol:Methanol (3:1), and the process referred to as Protocol 1B is a 15 second treatment with cold Carnoys {3:1 v/v, methanol:glacial acetic acid). Both of these post-fixation treatments are followed by air drying prior to the start of the FISH process.

Sample Preparation and Fixation
1) Centrifuge cells through PBS (Sigma P-4417) spinning for 5 min at approximately 300×gravity using a cell centrifuge.
2) Air dry for at least 10 min. no longer than 60 min.
3) Fix in fresh (3:1 v/v) Ethanol:Methanol for 10 min,
4) Air-dry slide.
5) Incubate on bench overnight.
6) Store frozen with desiccant.

Post-fixation Protocol 1A
7) Soak in fresh (3:1) Ethanol:Methanol for 15 seconds at room temperature.
8) Air-dry slide for at least 10 min.

Post-fixation Protocol 1B
7) Soak in fresh, cold Carnoys (3:1 v/v Ethanol:Glacial Acetic Acid at freezer temperature) for 15 seconds.
8) Air-dry slide for at least 10 min.

Hybridization
9) Apply 10 µl of probe/buffer cocktail to a sample area of 18 to 22 mm in diameter.
10) Apply a round coverslip to the sample area to distribute the cocktail across the sample.
11) Heat slide to 100° C. for 90 to 110 sec.
12) Incubate slide at 42° C. for 30 min.

Post-Hybridization Wash (all washing steps are at 42° C.)
13) Soak slide (with coverslip) for 1 min in 1/10 dilution of 20×SSC (1×SSC equals 0.15 M NaCl, 0.015 M sodium citrate).
14) Remove coverslip
15) Soak slide for 3 min in 1/10 dilution of 20×SSC
16) Transfer the slide to the first of four Coplin jars all containing 1/100 dilution of 20×SSC (0.0339 M Na$^+$) and soak for 30 seconds
17) Repeat the above step subsequently with the second through fourth Coplin jars with 1/100 dilution of 20×SSC
18) Air-dry slide
19) Apply mounting medium (VECTASHIELD, Vector Laboratories, Inc., Burlingame, Calif. (99% glycerol)) with DAPI
20) Apply 22 mm coverslip, view by epifluorescent microscopy The resulting slides may be stored in a light-tight container, either refrigerated or frozen, and the labeling has been found stable for at least 3 months.

Protocol 2: Repeat FISH (ReFISH)

Another adaptation of inventive FISH chemistry is a process referred to as ReFISH (repeat FISH). This is a repetitive process that allows the performance of several rounds of FISH analysis on the same sample, using different probe sets for each round of FISH analysis. Protocol 1, post-fixed as described in Protocol 1B using lymphocytes, is the sample preferably used for ReFISH. Before each subsequent hybridization reaction, the sample is processed through an alcohol dehydration series. The sample denaturation step of the first reaction is modified in the second and each subsequent FISH reaction, bringing the sample in probe/hybridization buffer cocktail to 70° C., which reverses any non-specific annealing of the single stranded oligonucleotide probe to the previously denatured sample DNA prior to 42° C. hybridization step.

Sample Preparation for ReFISH (for synthetic probes 20 to 35 bases in length)
1) Remove coverslip from sample by soaking the slide for 1 min in 1/10 dilution of 20×SSC.
2) If the coverslip hasn't fallen off, carefully remove it by lifting it off the sample
3) Before the sample dries, process the sample through the following series of ethanol:water solutions:
   a) Soak slide for 1 min in 50% ethanol
   b) Soak slide for 1 min in 70% ethanol
   c) Soak slide for min in 85% ethanol
   d) Soak slide for 1 min in 100% ethanol
4) Air-dry for at least 10 min Hybridization
5) To the air-dried sample, apply 10 µl of probe/hybridization buffer cocktail to a sample area of 18 to 22 mm in diameter
6) Apply a round coverslip to the sample area to distribute the cocktail across the sample
7) Heat the sample at 70° C. for 90 to 110 sec.
8) Incubate the sample at 42° C. for 30 min Post-Hybridization Wash
9) The post-hybridization wash protocol is outlined in Protocol 1

Protocol 3: Uncultured Amniocyte Hybridization

Amniocytes were processed as outlined below. Uncultured amniocytes were deposited on a slide by cytocentrifugation. The slides were air dried and kept at room temperature. The hybridization reaction for uncultured amniocytes differed from that for lymphocytes by having a hybridization time of 75 minutes and having the post-hybridization washes augmented with non-ionic Igepal-CA 630. The addition of detergent to post-hybridization washes was found to decrease non-specific fluorescent background.

Sample Preparation
1) Cells were pelleted from 5 ml of amniotic fluid at 450×g for 10 min
2) The cell pellet was re-suspended in 1 ml of PBS
3) Cell density was determined by hemocytometer counts with phase-contrast microscopy
4) Cells were deposited on the slide by adding approximately 20,000 cells to 0.5 ml of PBS in the cytocentrifuge well, centrifuging the sample at 2000 RPM (450×g) for 5 min
5) The final sample diameter was approximately 7 mm
6) Sample was air-dried overnight at room temperature (approximately 22° C.)
7) Sample was stored at room temperature in a slide folder Hybridization 8) Apply 5 μl of probe/hybridization buffer cocktail to the sample area
9) Apply a round coverslip to the sample area to distribute the cocktail across the sample
10) Heat slide to 100° C. for 90 to 110 seconds
11) Incubate slide at 42° C. for 75 minutes Post-Hybridization Wash (all washing steps are at 42° C.)

12) Soak slide (with coverslip) for 1 min in 1/10 dilution 20×SSC wash with Igepal-CA 630
13) Remove coverslip
14) Place slide in 1/10 dilution of 20×SSC wash with Igepal-CA 630, soak for 3 min
15) Transfer and soak the slide for 30 seconds in the first of four Coplin jars, all containing 1/100 dilution of 20×SSC (0.0195 M Na⁺) with Igepal-CA 630
16) Repeat the step 15 with second through fourth Coplin jars containing 1/100 dilution of 20×SSC with Igepal-CA 630
17) Air-dry slide
18) Apply mounting medium (VECTASHIELD, Vector Laboratories, Inc., Burlingame, Calif. (99% glycerol)) with DAPI
19) Apply coverslip, view by epifluorescence microscopy Protocol 4: Metaphase Chromosome Hybridization The inventive glycerol-based hybridization methodology has been successfully employed with metaphase chromosomes using synthetic oligonucleotide probe sets for X/Y, 13 and 21, 18 and Y with 21 specific probes from Aprogenex, Inc. utilizing the below described Protocol 4.

Sample Preparation

1) The metaphase-arrested cells were fixed in Carnoys's.
2) A glass slide was soaked in absolute methanol for at least 5 sec.
3) The slide was then dipped in distilled water and immediately placed horizontal on a flat surface.
4) While still wet with distilled water, one to two drops of cells in Carnoys's fixed metaphase cell preparation were deposited onto the slide.
5) The slide was set for 15–20 sec. And then placed at a sharp angle to drain off excess fluid, and the back of the slide wiped dry.
6) The slide was then allowed to dry for 10 min.
7) The slide was then incubated in a humid box for 35 min.

Hybridization 8) 5 μl of probe/hybridization buffer cocktail was applied to the sample area on the slide.
9) A round coverslip was applied to the sample area to distribute the cocktail across the sample
10) The slide was heated to 100° C. for 90 to 110 seconds to denature the sample.
11) The slide was incubated at 42° C. for 30 to 90 minutes to hybridize the sample.

Post-Hybridization Wash (all washing steps are at 42° C.)

12) Soaked slide (with coverslip) for 1 min in 1/10 dilution Wash Stock A
13) Removed coverslip
14) Placed slide in 1/10 dilution of 20×SSC with Triton X-100 and soaked for 3 min
15) Transferred the slide to 1/100 dilution of 20×SSC and soaked the slide for 2 min
16) Transferred slide back to the 1/10 dilution of 20×SSC with Triton X-100 and soaked for 30 sec.
17) Transferred slide to a first of four Coplin jars, each containing a 1/200 dilution of 20×SSC, and soaked for 30 minutes.
18) Step 17 was repeated, sequentially, with second through fourth Coplin jars containing the 1/20 dilution of 20×SSC wash.
17) The slide was then air dried.
18) Mounting medium (VECTASHIELD, Vector Laboratories, Inc., Burlingame, Calif. (99% glycerol)) with DAPI and augmented 0.8 M NaCl, added as a stabilizing agent, was applied to the slide.
19) The sample was coverslipped and viewed by epifluorescence microscopy.

Results

Lymphocyte FISH

Figure 2:
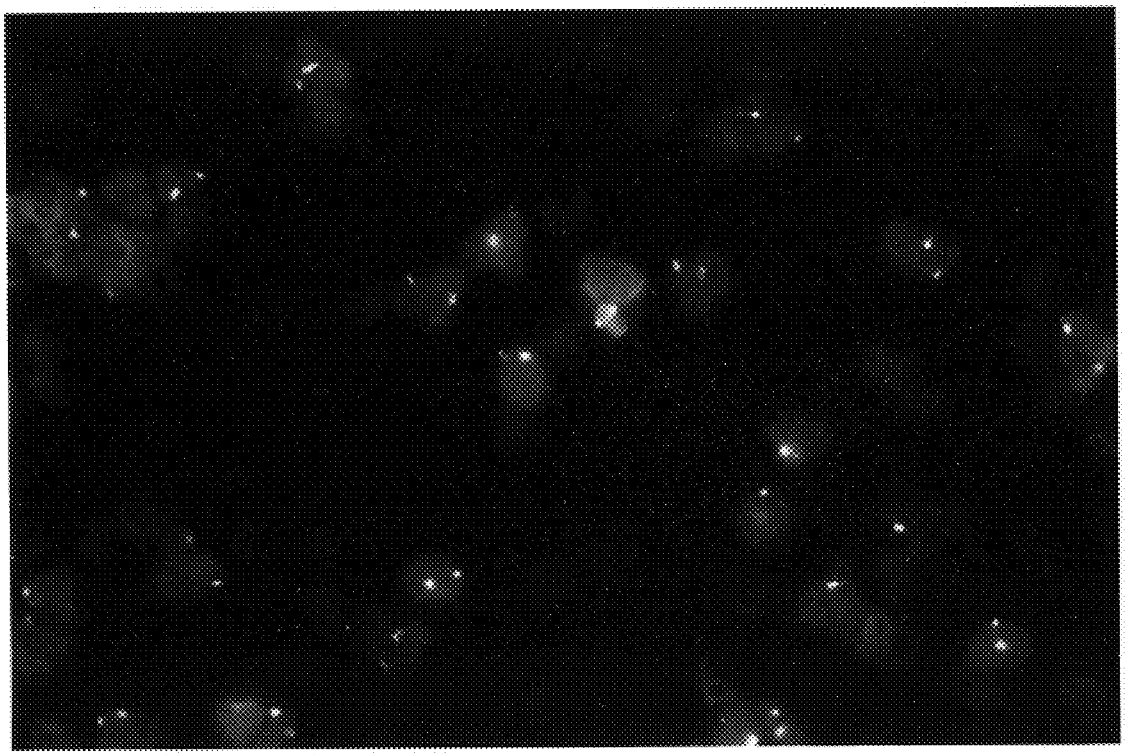
FIG. 2 is a photomicrograph illustrating lymphocytes labeled with fluorescent probes for X and Y chromosomes in accordance with the present invention.
Figure 3:
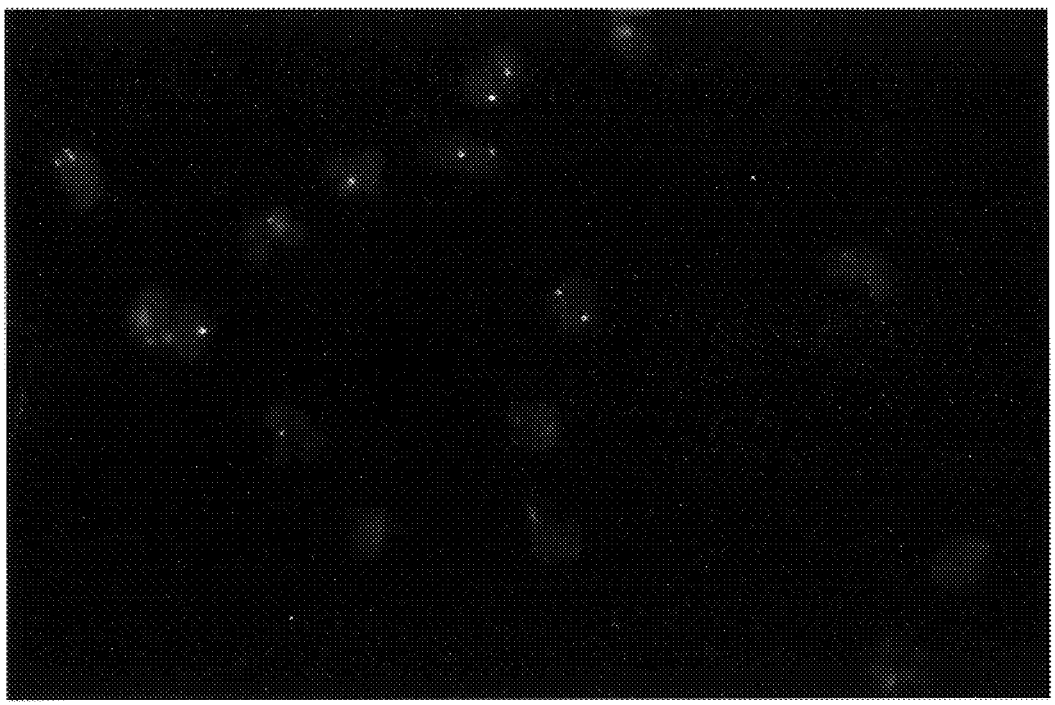
FIG. 3 is a photomicrograph illustrating lymphocytes labeled with fluorescent probes for chromosome 18 in accordance with the present invention.

The results of cells processed through protocol 1A are illustrated in FIGS. 1 through 3. These peripheral lymphocytes are post-fixed in Ethanol:Methanol as described in Protocol 1A. These interphase cells are labeled by glycerol-directed FISH. For these reactions, the labeling was easily seen at magnifications of 200× or greater.

Figure 4:
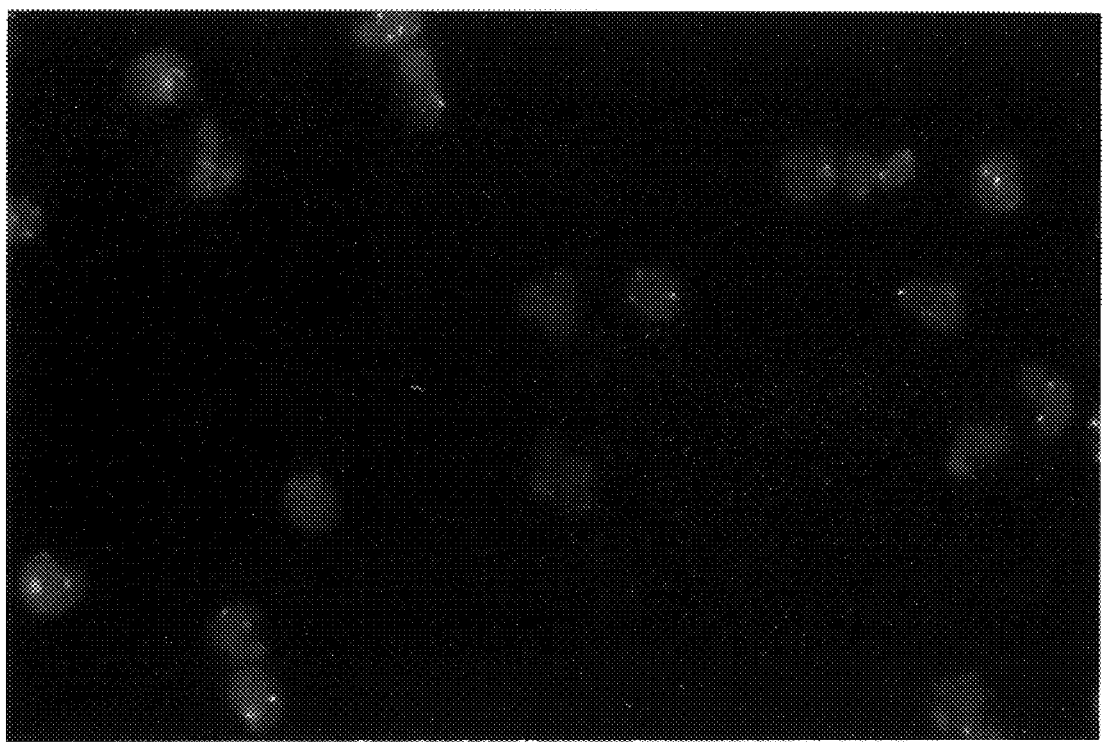
FIG. 4 is a photomicrograph illustrating lymphocytes labeled with fluorescent probes for chromosomes 13 and 21 in accordance with the present invention.
Figure 5:
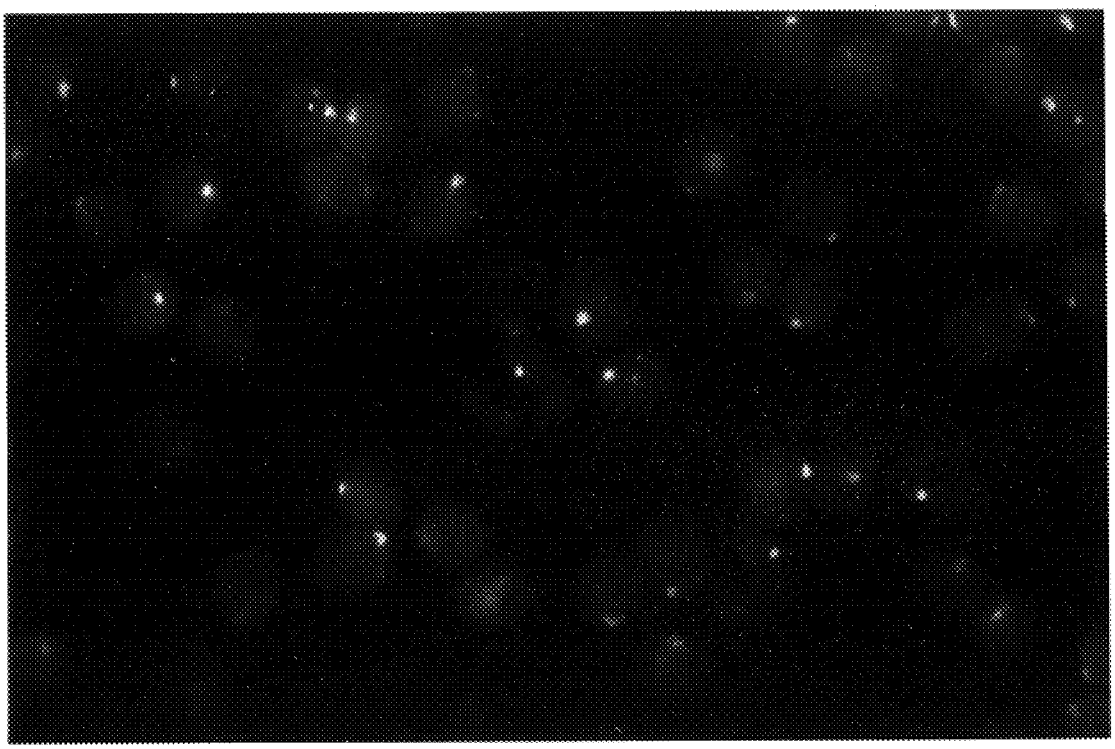
FIG. 5 is a photomicrograph illustrating interphase nuclei from peripheral blood lymphocytes labeled with fluorescent probes for X and Y chromosomes in accordance with an alternative preferred methodology of the present invention.
Figure 6:
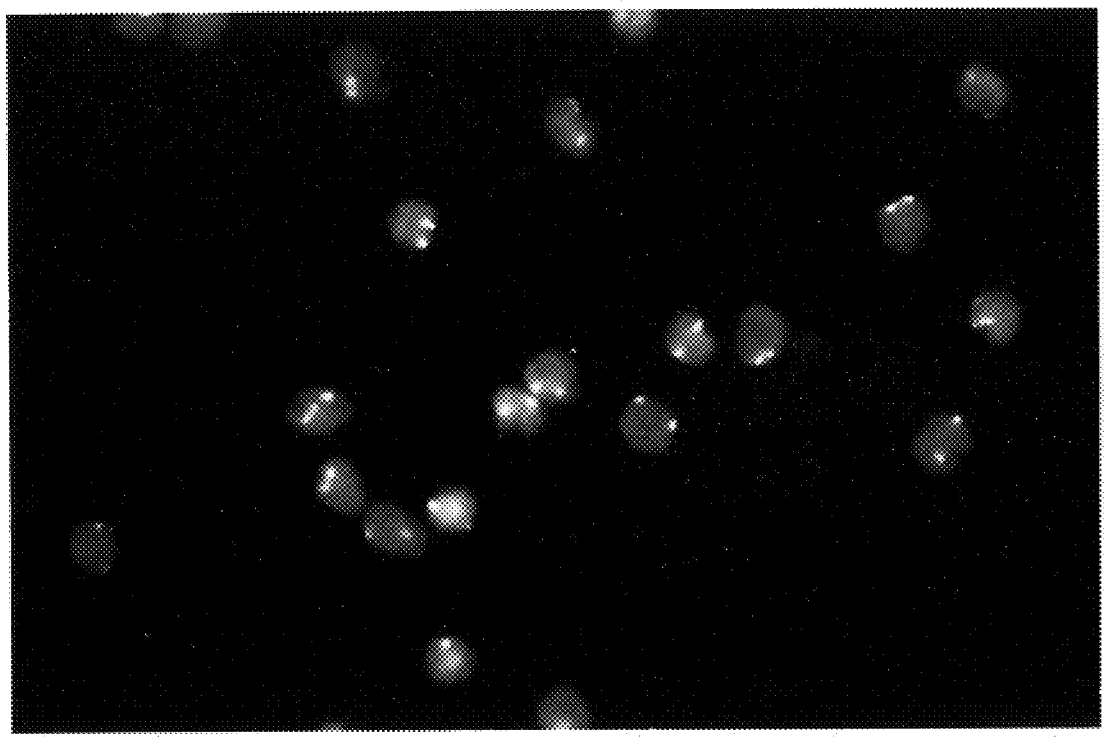
FIG. 6 is a photomicrograph illustrating interphase nuclei from peripheral blood lymphocytes labeled with fluorescent probes for chromosome 18 in accordance with an alternative preferred methodology of the present invention.

The results of glycerol-directed FISH of interphase nuclei from peripheral blood lymphocytes are illustrated in FIGS. 4 through 6. These nuclei were produced by treatment with Carnoys (Protocol 1B). For all of these reactions, the labeling is easily seen at magnifications of 200× or greater. FIGS. 4–6 were taken 3 months after the FISH labeling reaction, illustrates the stability of the inventive labeling reactions in the glycerol-NaCl mounting medium.

ReFISH

The results of glycerol-directed FISH and ReFISH of interphase nuclei from peripheral blood lymphocytes are illustrated in FIGS. 7 through 10. The sample is post-fixed by protocol 1B prior to the first FISH reaction. The first FISH reaction is the process outlined in Protocol 1. For all of these reactions, the labeling was easily seen at magnifications of 200× or greater except for the 21-specific probe where it was seen at magnifications of 600× or greater.

Figure 7:
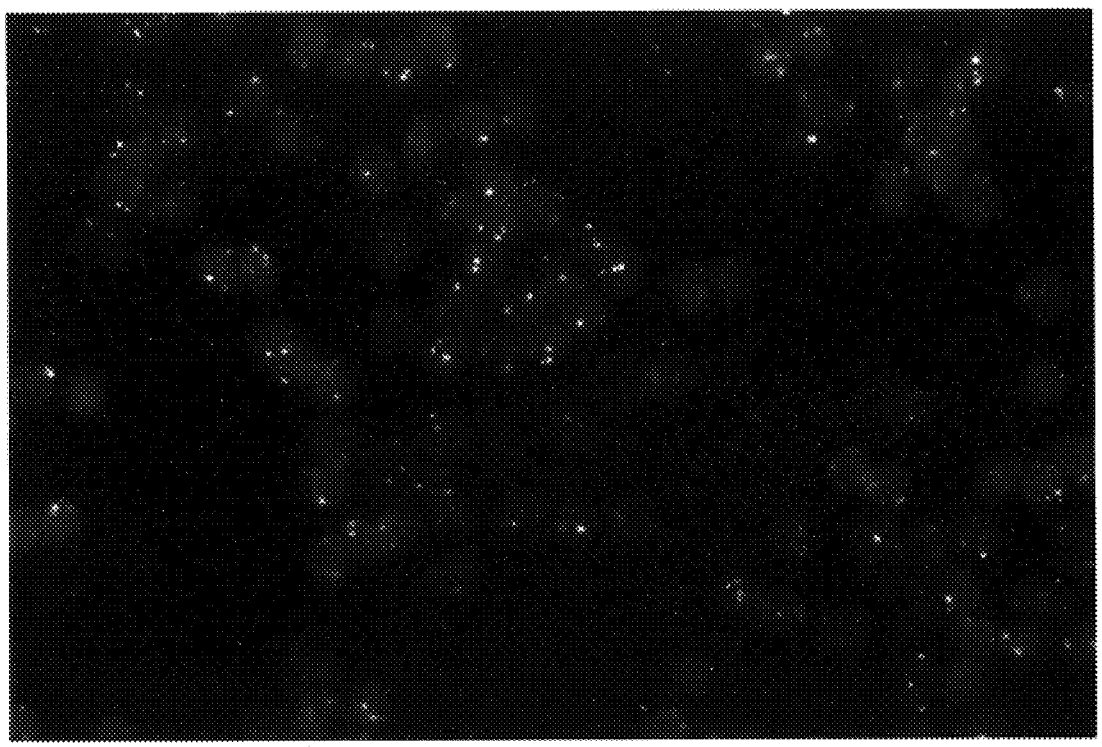
FIG. 7 is a photomicrograph illustrating interphase nuclei from peripheral blood lymphocytes labeled with fluorescent probes for chromosomes 13 and 21 in accordance with an alternative preferred methodology of the present invention.
Figure 8:
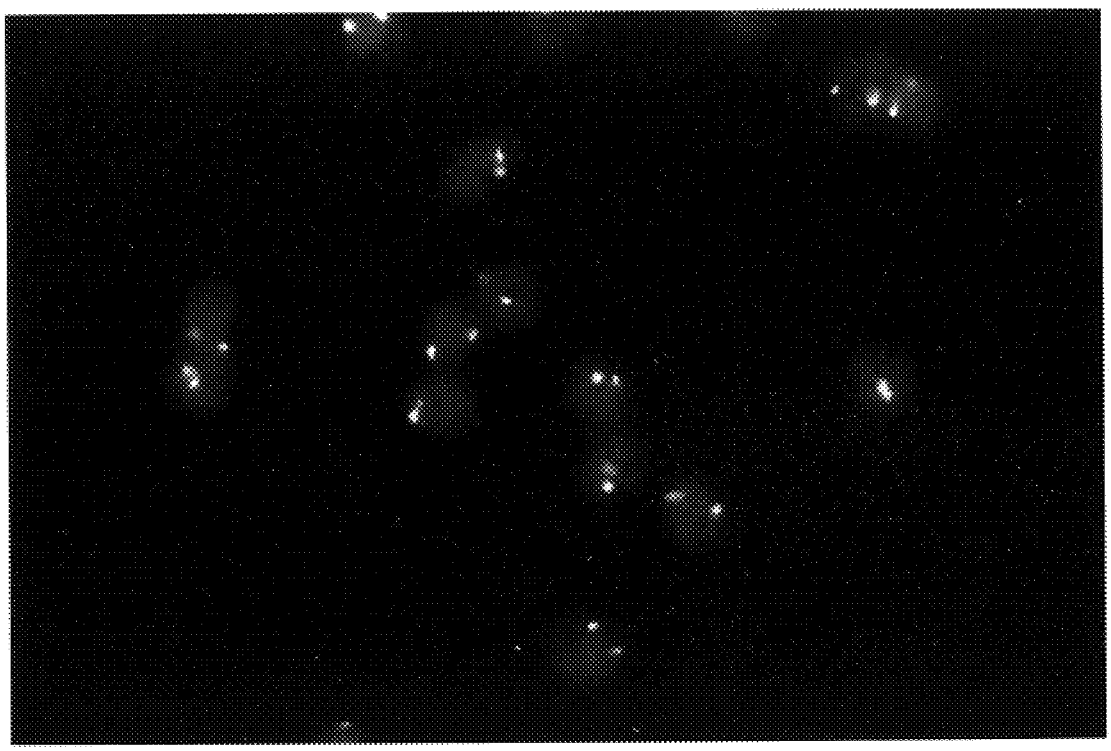
FIG. 8 is a photomicrograph illustrating the results of the inventive FISH methodology using interphase nuclei from peripheral blood lymphocytes labeled with fluorescent probes for X and Y chromosomes.
Figure 9:
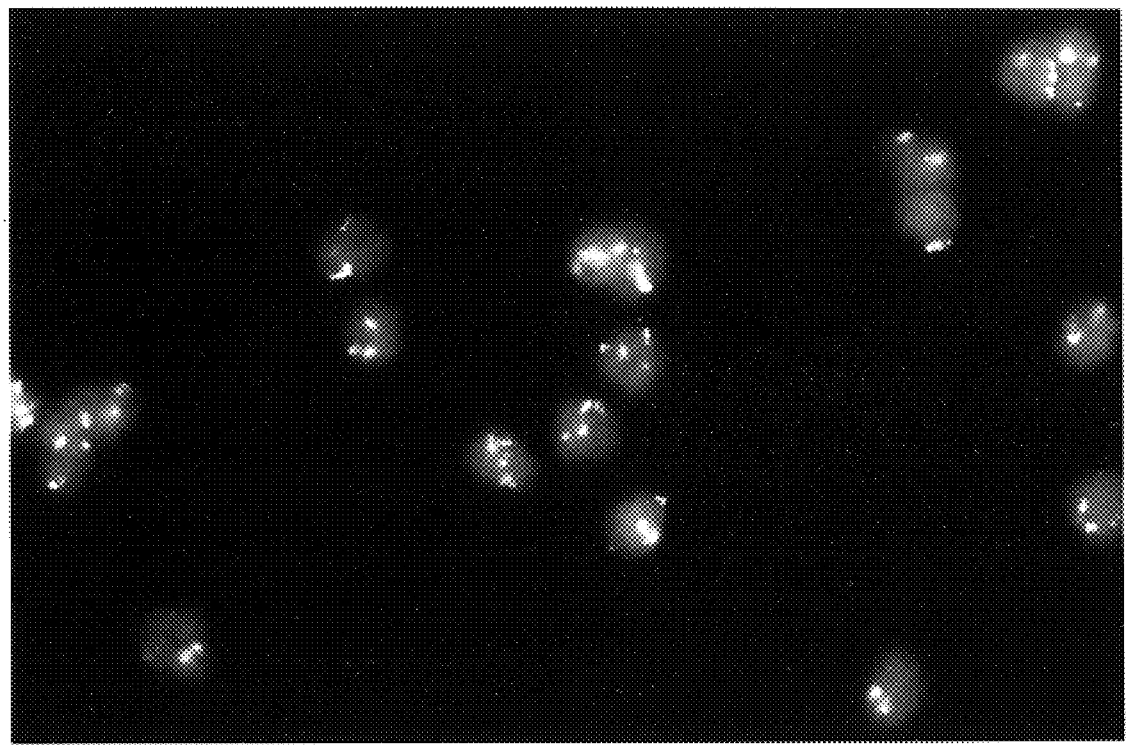
FIG. 9 is a photomicrograph illustrating the results of the inventive ReFISH methodology using the sample illustrated in FIG. 8 and additionally labeled with fluorescent probes for chromosomes 13 and 21.
Figure 10:
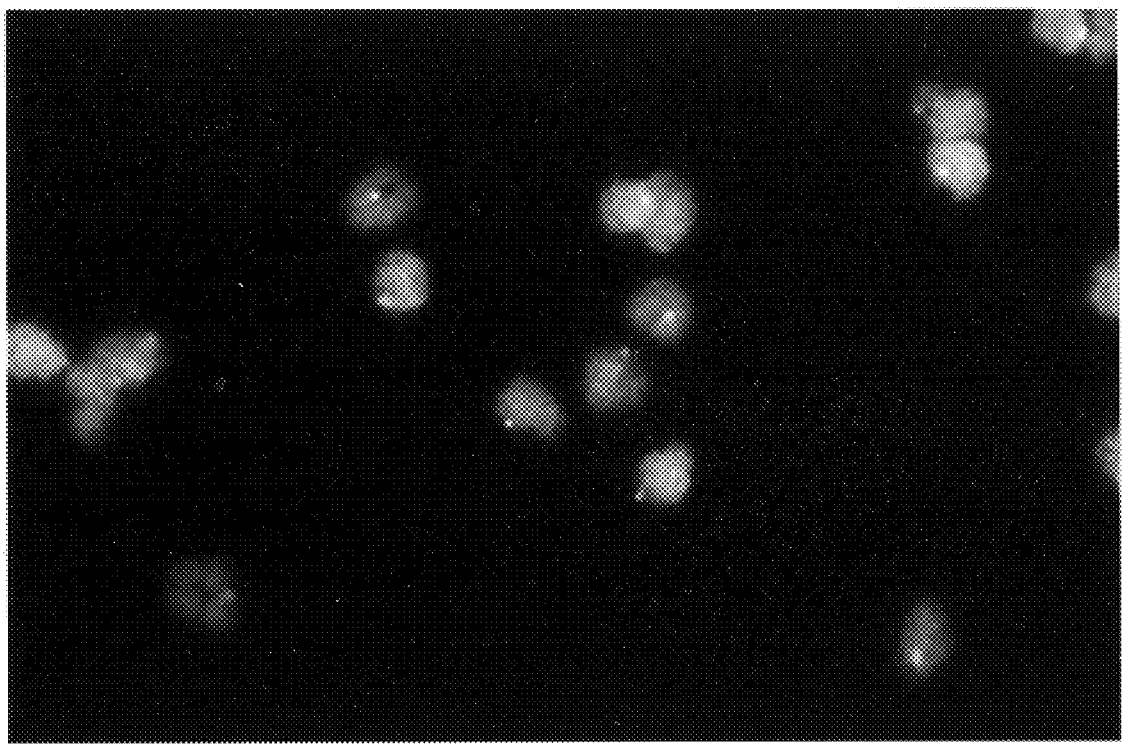
FIG. 10 is a photomicrograph illustrating the results of using a second ReFISH methodology of the sample illustrated in FIG. 8 and FIG. 9, additionally labeled with fluorescent probes for the centromeric regions of chromosome Y and locus specific probes for chromosome 21.

The hybridization efficiency for the first FISH reaction and the last ReFISH reaction are reported in Table 1, below. These results show that hybridization efficiency for the same sample, after the fourth FISH reaction, did not differ from that observed for chromosomes X and Y labeled in the first reaction. This suggests that the loss of chromosomal target sequences is insignificant between the repeated FISH processing steps. FIGS. 7 and 10 illustrate this as well. In addition, both nuclear and signal morphology were retained through four rounds of FISH, as comparison of FIGS. 7 and 10 shows.

TABLE 1

Hybridization efficiency of a sample subjected to four rounds of FISH. First round with X and Y probe sets and the fourth round with chromosome 18-specific probe set.

|  | X/Y | 0/X | 0/Y | 0/0 |
|---|---|---|---|---|
| First Round: Chromosomes X and Y, centromere probes | 243/245 (99.2%) | 2/245 (0.8%) | 0 | 0 |
|  | 18/18 | 18/0 | 0/0 | >18/18 |

TABLE 1-continued

Hybridization efficiency of a sample subjected to four rounds of FISH. First round with X and Y probe sets and the fourth round with chromosome 18-specific probe set.

|  | X/Y | 0/X | 0/Y | 0/0 |
|---|---|---|---|---|
| Fourth Round: Chromosome 18, centromere probe | 245/245 (100%) | 0 | 0 | 0 |

Uncultured Amniocytes

Figure 11:
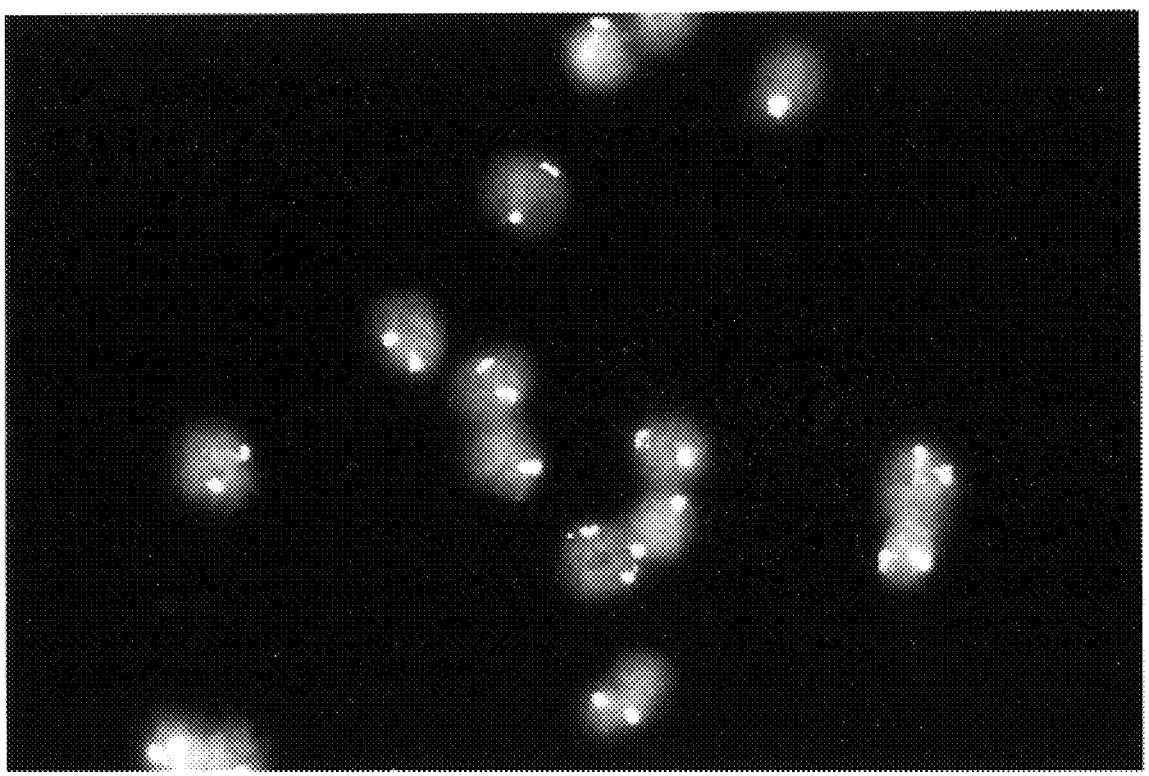
FIG. 11 is a photomicrograph illustrating the results of using a third ReFISH methodology using the sample illustrated in FIGS. 8–10, and additionally labeled with fluorescent probes specific for chromosome 18.
Figure 12:
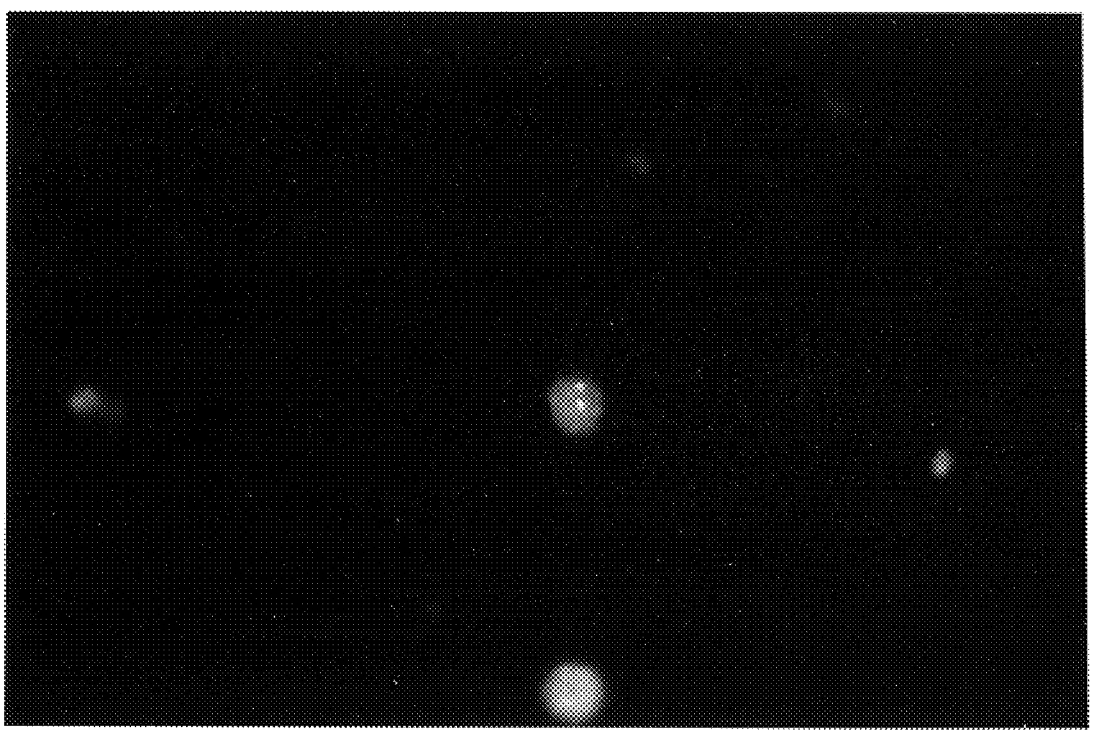
FIG. 12 is a photomicrograph illustrating uncultured amniocytes labeled with fluorescent probes for X and Y chromosomes in accordance with the present invention.
Figure 13:
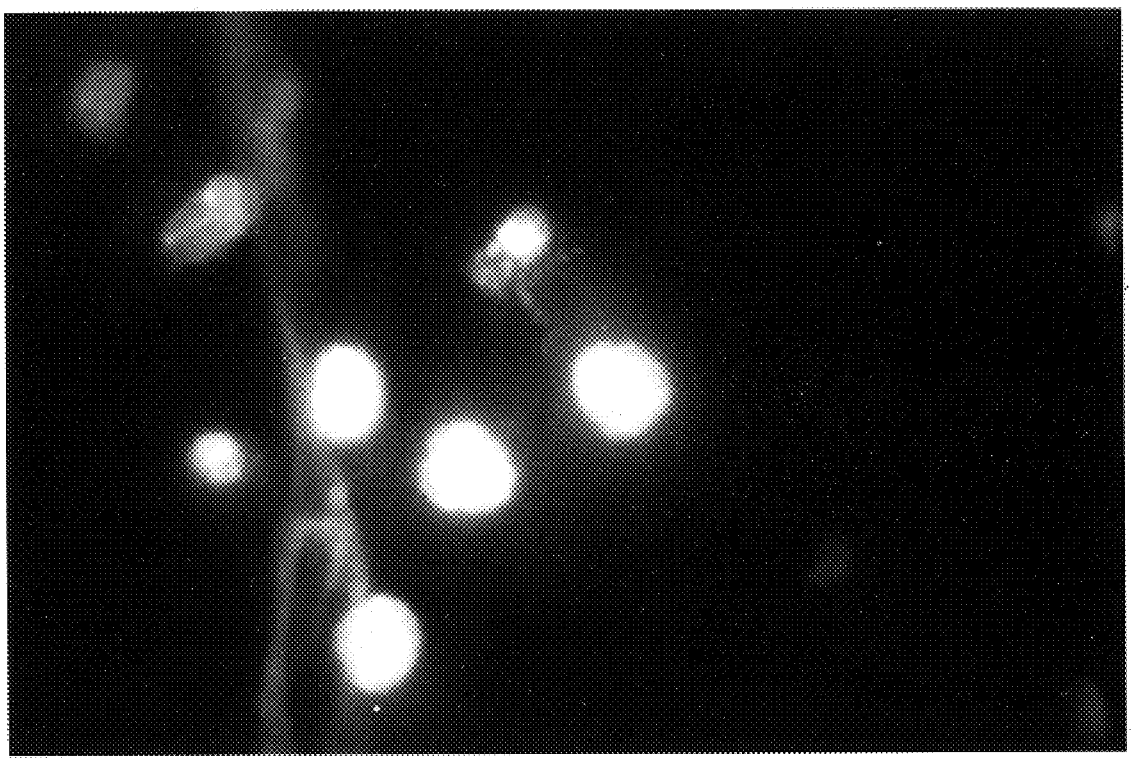
FIG. 13 is a photomicrograph illustrating uncultured amniocytes labeled with fluorescent probes for chromosome 18 in accordance with the present invention.
Figure 14:
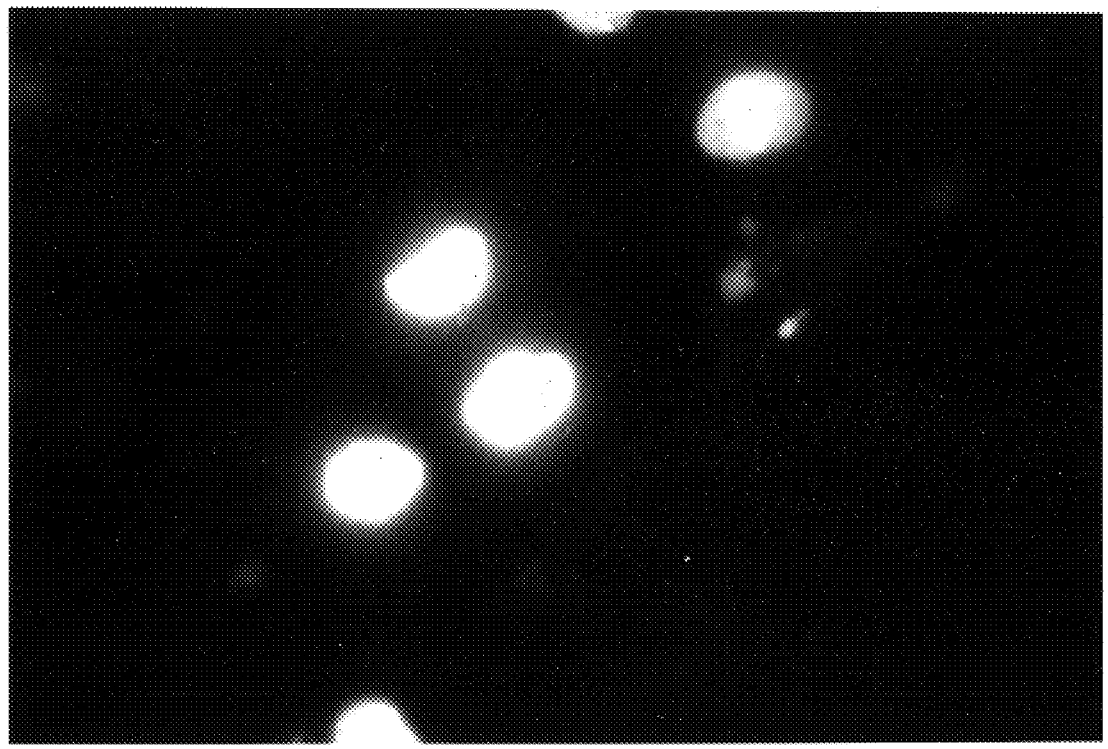
FIG. 14 is a photomicrograph illustrating uncultured amniocytes labeled with fluorescent probes for chromosomes 13 and 21 in accordance with the present invention.

The result of glycerol-directed FISH with uncultured amniocytes are illustrated in FIGS. 11 through 13. The hybridization efficiency of the XY hybridization is reported in Table 2, below. The hybridization efficiency for the X and Y labeling is 94.8% of cells with intact nuclei. These cell preparations are crude and are not washed prior to deposition on the slide.

TABLE 2

Hybridization efficiency of an uncultured amniocyte sample subjected to FISH using centromere probe sets for chromosomes X and Y.

|  | X/Y | 0/X | 0/Y | Multiple signal | 0/0 |
|---|---|---|---|---|---|
| Amniocytes | 327/345 (94.8%) | 0 | 0 | 16/345 (4.6%) | 2/345 (0.6%) |

Metaphase Chromosome Sample

Except for the 21 specific probes, all probes gave distinct signals per spread with very faint non-specific and non-target background.

While the present invention has been described with reference to its preferred embodiments and the foregoing examples, those of ordinary skill in the art will understand and appreciate that the scope of the present invention is not limited by the foregoing examples or reaction conditions, but only by the claims appended hereto.

What is claimed is:

1. An in-situ hybridization method, comprising the steps of:
   a. isolating a cell population,
   b. denaturing nucleic acid sequences within cells of the cell population,
   c. hybridizing labeled, synthetic oligonucleotide probes having no more than 75 bases with target denatured nucleic acid sequences within the cells in the presence of a glycerol-based hybridization medium at temperatures between 37° C. and 47° C. to form labeled hybridized complexes, and
   d. washing the labeled hybridized complexes at temperatures between 37° C. and 47° C. wherein the washing is performed at temperatures substantially the same as the hybridization temperature in step c.

2. The in-situ hybridization method according to claim 1, wherein step c further comprises the step of adding to the glycerol-based hybridization medium a reducing agent selected from the group consisting of dithiothreitol, mercaptoethanol, dithioerythritol and tris(2-carboxyethyl) phosphine.

3. A labeled hybridized complex which is the product of claim 1, step d, wherein the labeled hybridized complex comprising the labeled, synthetic oligonucleotide probe having no more than 75 bases annealed to the target denatured nucleic acid sequence is stable for a period of time greater than thirty days.

4. A method of in-situ hybridization using labeled, synthetic oligonucleotide probes, comprising the step of hybridizing the labeled, synthetic oligonucleotide probes with nucleotide sequences under temperature conditions determined according to the formula:

$$T_{hyb}=[(16.6 \log (Na^+)+0.41 \ (\% \ G+\% \ C)+81.5)-500/L]-X$$

wherein, $Na^+$ is equal to the concentration of sodium in the hybridization solution, % G is equal to the percent of guanine bases in one of the probe and target sequence, % C is equal to the percent of cytosine bases in one of the probe and target sequence, L is the number of nucleic acids in one of the probe or target sequence and X is an integer between about 18 and 30.

5. The method of in situ hybridization according to claim 4, further comprising the step of washing a hybrid resulting from the hybridization step with a wash solution comprising sodium ions, the washing step being conducted at a temperature below the temperature of melting of the hybrid and determined according to the formula:

$$T_{wash}=[(16.6 \log (Na^+)+0.41 \ (\% \ G+\% \ C)+81.5)-500/L]-Y$$

wherein, $Na^+$ is equal to the concentration of sodium in the wash solution, % G is equal to the percent of guanine bases in one of the probe or the target sequence, % C is equal to the percent of cytosine bases in one of the probe and the target sequence, L is the number of nucleic acids in one of the probe or the target sequence, and Y is an integer between 6 and 30.

6. The method of claim 3, further comprising the steps of:
   a. dehydrating a first labeled hybridized complex obtained from claim 3;
   b. hybridizing at least a second labeled synthetic oligonucleotide probe having no more than 75 bases with the first labeled hybridized complex from step a, in the presence of a glycerol-based hybridization medium at temperatures between 37° C. and 47° C. to form at least a second labeled hybridized complex;
   c. washing the at least a second labeled hybridized complex at temperatures between 37° C. and 47° C. wherein the washing is performed at temperatures substantially the same as the hybridization temperature in step b;
   d. repeating steps b and c for successive cycles to form additional labeled hybridized complexes as desired.

7. The method according to claim 6, further comprising the step of adding to the glycerol-based hybridization medium a reducing agent selected from the group consisting of dithiothreitol, mercaptoethanol, dithioerythritol and tris (2-carboxyethyl)phosphine.

8. A labeled hybridized complex which is the product of claim 6, step c, wherein the at least a second labeled hybridized complex comprising the at least a second labeled synthetic oligonucleotide having no more than 75 bases probe annealed to the labeled hybrid complex is stable for a period of time greater than thirty days.

9. The method of claim 6, further comprising the step of hybridizing the at least a second labeled, synthetic oligonucleotide probe with nucleotide sequences under temperature conditions determined according to the formula:

$$T_{hyb}=[(16.6 \log (Na^+)+0.41 \ (\% \ G+\% \ C)+81.5)-500/L]-X$$

wherein, $Na^+$ is equal to the concentration of sodium in the hybridization solution, % G is equal to the percent of guanine bases in one of the probe and target sequence, % C is equal to the percent of cytosine bases in one of the probe and target sequence, L is the number of nucleic acids in one of the probe or target sequence and X is an integer between about 18 and 30.

10. The method according to claim 9, further comprising the step of washing the labeled hybridized complex resulting from the hybridization step with a wash solution comprising sodium ions, the washing step being conducted at a temperature below the melting temperature of the hybrid and determined according to the formula:

$$T_{wash} = [(16.6 \log (Na^+) + 0.41 (\% G + \% C) + 81.5) - 500/L] - Y$$

wherein, $Na^+$ is equal to the concentration of sodium in the hybridization solution, % G is equal to the percent of guanine bases in one of the probe and target sequence, % C is equal to the percent of cytosine bases in one of the probe and target sequence, L is the number of nucleic acids in one of the probe or target sequence and Y is an integer between 6 and 30.

* * * * *